United States Patent
Kocabas et al.

(10) Patent No.: US 11,602,546 B2
(45) Date of Patent: Mar. 14, 2023

(54) COMBINATION INHIBITING MEIS PROTEINS

(71) Applicant: YEDİTEPE ÜNİVERSİTESİ, Istanbul (TR)

(72) Inventors: Fatih Kocabas, Istanbul (TR); Raife Dilek Turan, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 841 days.

(21) Appl. No.: 16/347,581

(22) PCT Filed: Sep. 25, 2017

(86) PCT No.: PCT/TR2017/050445
§ 371 (c)(1),
(2) Date: May 5, 2019

(87) PCT Pub. No.: WO2018/203855
PCT Pub. Date: Nov. 8, 2018

(65) Prior Publication Data
US 2019/0343886 A1 Nov. 14, 2019

(30) Foreign Application Priority Data

Nov. 16, 2016 (TR) .................. 2016/16602

(51) Int. Cl.
| | |
|---|---|
| A61K 35/28 | (2015.01) |
| A61K 31/095 | (2006.01) |
| A61K 31/655 | (2006.01) |
| A61K 38/18 | (2006.01) |
| A61K 38/19 | (2006.01) |
| A61K 38/28 | (2006.01) |
| A61K 38/38 | (2006.01) |
| A61K 38/40 | (2006.01) |
| A61K 31/15 | (2006.01) |
| A61K 31/167 | (2006.01) |

(52) U.S. Cl.
CPC ............ *A61K 35/28* (2013.01); *A61K 31/095* (2013.01); *A61K 31/655* (2013.01); *A61K 38/18* (2013.01); *A61K 38/196* (2013.01); *A61K 38/28* (2013.01); *A61K 38/385* (2013.01); *A61K 38/40* (2013.01); *A61K 31/15* (2013.01); *A61K 31/167* (2013.01)

(58) Field of Classification Search
CPC ..................................................... A61K 35/28
See application file for complete search history.

(56) References Cited

U.S. PATENT DOCUMENTS

2015/0353890 A1 12/2015 Bernstein et al.

FOREIGN PATENT DOCUMENTS

| EP | 2236131 A2 | 10/2010 |
| WO | 2015148716 A1 | 10/2015 |

OTHER PUBLICATIONS

Kocabas et al., "Meis1 regulates the metabolic phenotype and oxidant defense of hematopoietic stem cells", Blood, vol. 120 No. 25, Dec. 13, 2012 (Year: 2012).*
"MethoCultTM GF M3434", StemCell Technologies, Jul. 8, 2016 (Year: 2016).*
"MSCs: the 'other' bone marrow stem cells", EuroStem Cell, Nov. 30, 2016 (Year: 2016).*
Mackenzie et al., "The effect of pH on growth, protein synthesis, and lipid-rich particles of cultured mammalian cells", J Biophys Biochem Cytol., Jan. 9, 1961 (Year: 1961).*
Merve Aksoz et al. "Emerging Roles of Meis1 in Cardiac Regeneration, Stem Cells and Cancer". Current Drug Targets, vol. 19, No. 2: 181-190. Jan. 18, 2018. XP055532962, US.
Anonymous. "4-[2-(Benzylamino)-2-oxoethoxy]-N-(2,3-dimethylpheny) benzamide | C24H24N2O3—Pubchem". Pubchem. Jul. 10, 2005. XP055533447. Retrieved from the Internet: URL: https://pubchem.ncbi.nlm.nih.gov/compound/1191314#section= Top [retrieved on Dec. 12, 2018].
Anonymous. "4-Hydroxy-N'-[(Z)—(2-oxonaphthalen-1-ylidene)methyl]benzohydrazide | C18H14N2O3—Pubchem". Pubchem. Jul. 28, 2005. XP055533480. Retrieved from the Internet: URL: https://pubchem.ncbi.nlm.nih.gov/compound/5717209#section= Top [retrieved on Dec. 12, 2018].
Bisaillon Richard et al. "Identification of MEIS-PBX inhibitors as potential anti-leukemic agents using a high-throughput bret-based assay". Experimental Hematology, vol. 41, No. 8. 2013. XP028688191.

* cited by examiner

Primary Examiner — Daniel R Carcanague
Assistant Examiner — Gillian A Hutter
(74) Attorney, Agent, or Firm — Bayramoglu Law Offices LLC

(57) ABSTRACT

A composition inhibiting MEIS proteins. The MEIS proteins are effective in proliferation of hematopoietic stem cells. A formulation capable of easily passing through the cell membrane and perform its activity in the cell, and can inhibit MEIS activity in a dose dependent manner. The combination includes isolated cells, medium, growth factors and MEISi inhibitor. The isolated cells are isolated from mouse bone marrow, human bone marrow and human umbilical cord blood. The medium has a pH value of 7.2 and contains bovine serum albumin, recombinant insulin, transferrin, 2-mercaptoethanol and IMDM medium. The growth factors are hematopoietic stem cell factor SCF, fetus liver tyrosine kinase-3 ligand Flt3L, and thrombopoietin. A chemical formula of the MEISi-1 is 4-[2-(benzylamino)-2-oxoethoxy]-N-(2,3-dimethylphenyl) benzamide. A chemical formula of MEISi-2 is 4-hydroxy-N'-[(Z)-(2-oxonaphthalen-1-ylidene)methyl] benzohydrazide.

20 Claims, 10 Drawing Sheets

COMBINATION INHIBITING MEIS PROTEINS

CROSS REFERENCE TO THE RELATED APPLICATIONS

This application is the national phase entry of International Application No. PCT/TR2017/050445, filed on 25, Sep. 2017, which is based upon and claims priority to Turkish Patent Application No. 2016/16602, filed on 16, Nov. 2016, the entire contents of which are incorporated herein by reference.

TECHNICAL FIELD

The present invention relates to a combination which inhibits MEIS proteins which are effective in the proliferation of hematopoietic stem cells (HSCs).

BACKGROUND

The most significant features of the hematopoietic stem cells (HSCs) are the self-renewal ability and ability to differentiate into a plurality of types of cells. By means of these abilities, HSCs can transform into all types of blood cells while also maintaining the regeneration capacity required for hematopoietic activity of the body in the future. HSCs are frequently used in HSC transplantations for treatment of hematological diseases thanks to their self-renewal abilities. However, even if suitable donors are found for these transplantations, the number of allogenic HSCs obtained from sources such as umbilical cord blood is not alone sufficient for an effective transplantation. Therefore, studies for ex vivo proliferation of HSCs are required for such therapeutic applications. Furthermore, in hematopoietic cells, after gene regulation technologies, single cell selection and proliferation of these cells are required.

In some applications in the literature, it is observed that deletion of HSC silencing genes in mice leads to proliferation of HSC. Meis1 protein is one of the most remarkable ones of these targets and appears as a therapeutic target in stem cell proliferation technologies.

MEIS proteins (Meis1, Meis2 and Meis3) are comprised of various domains. Pbx1 domain is effective in interaction and coactivation of Meis1 with Pbx1 protein. This domain is located at amino acids 69-194 at N terminus of Meis1 protein. Another important domain is transactivation domain which generally comprises C terminus including amino acids 335-390. Another important domain is the homeobox domain (also called homeodomain) after which these proteins are named. Size of this domain is about 62 amino acids in Meis 1 protein and includes amino acids 272-335. Meis1-specific nucleotide sequence of Meis1 protein in DNA enables it to bond to TGACAG. This bonding domain has a protein sequence which is protected and same in MEIS proteins, i.e. Meis1, Meis2 and Meis3 proteins. The facts that MEIS proteins bond to DNA through this domain and have Meis1-specific DNA binding nucleotide sequence makes homeodomain an ideal target for inhibitor studies.

MEIS proteins (Meis1, Meis2 and Meis3) belong to the Homeobox proteins family comprising TALE class homeodomain. Homeobox proteins are nuclear proteins and they mostly function as transcription factors. Meis1 protein also has the feature of inhibiting cardiomyocyte cell cycle in heart regeneration.

United States patent document no. US20150353890 relates to kits, compositions and methods required for expansion of embryonic hematopoietic stem cells and provision of the hematopoietic function to patients in need thereof.

European patent document no. EP2236131 discloses a method and composition for modulating the activity of sirtuin deacetylase proteins.

International patent document no. WO2015148716 discloses methods and compositions obtained for ex vivo expansion of human hematopoietic cells/progenitor cells.

SUMMARY

The objective of the present invention is to provide a combination inhibiting MEIS proteins (Meis1, Meis2 and Meis3) which are effective in proliferation of hematopoietic stem cells.

Another objective of the present invention is to provide a combination which can easily pass through the cell membrane and carry out its activity in the cell.

A further objective of the present invention is to provide a combination which inhibits activity of MEIS proteins in a dose-dependent manner.

Another objective of the present invention is to provide a combination which induces ex vivo mouse hematopoietic stem cell expansion.

Another objective of the present invention is to provide a combination which induces ex vivo human umbilical cord blood hematopoietic stem cell expansion.

Another objective of the present invention is to provide a combination which induces ex vivo human bone marrow and peripheral hematopoietic stem cell expansion.

A further objective of the present invention is to provide a combination which induces hematopoietic stem cell expansion after gene regulation in hematopoietic cells.

Another objective of the present invention is to provide a combination which enhances hematopoietic stem cell expansion by performing MEIS inhibition in in vivo preclinical studies.

Another objective of the invention is to provide a combination which reduces p21, Hif1a, Hif2a gene expressions.

A further objective of the present invention is to provide a combination which increases the number of GEMM (Granulocyte, Erythrocyte, Macrophage, Megakaryocyte) hematopoietic stem cell colonies more than 5 times.

Another objective of the present invention is to provide a combination which increases the number of erythrocyte progenitors.

Yet another objective of the present invention is to provide a combination which inhibits transcriptional activation of MEIS proteins.

BRIEF DESCRIPTION OF THE DRAWINGS

The present invention is a combination comprised of small molecules inhibiting MEIS proteins, which molecules are also effective in ex vivo and in vivo HSC proliferation.

Meis1, Meis2 and Meis3 proteins, which are the MEIS proteins that constitute the combination of the present invention, have made a significant contribution to the stem cell proliferation technologies required in stem cell transplantations.

The inhibitor which is disclosed in the present description and which constitutes the present invention is briefly named as "MEISi-1" and it refers to MEIS inhibitor-1.

Figure 1:
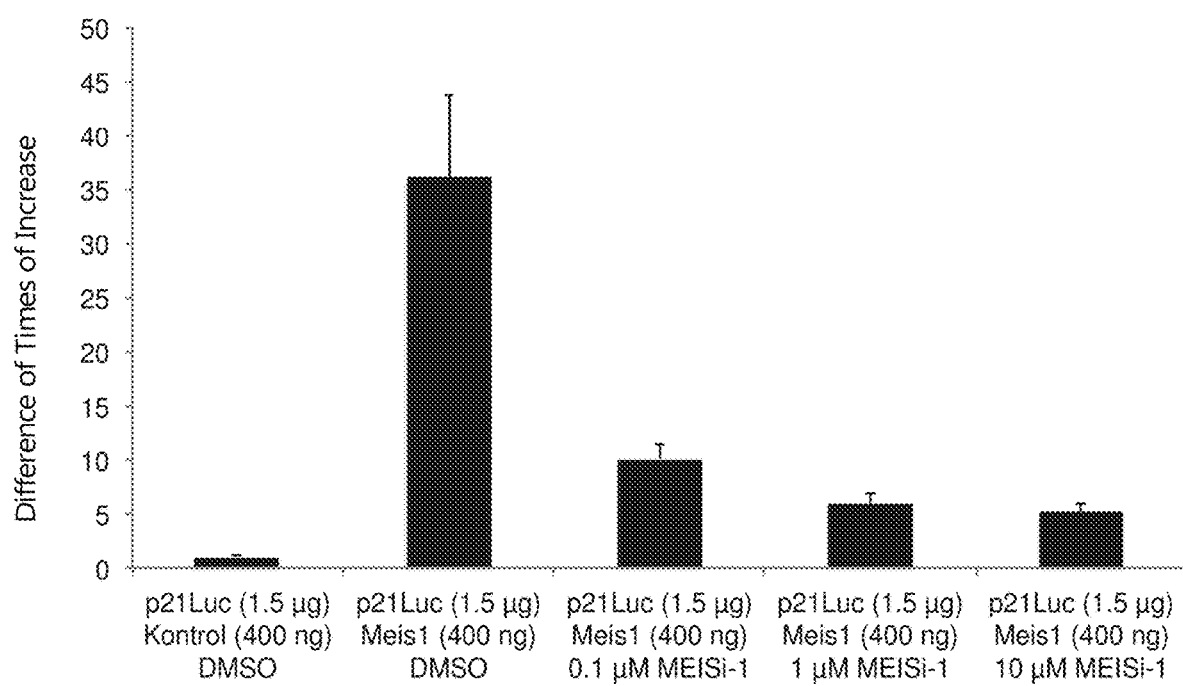

MEISi-2 refers to MEIS inhibitor-2. The figures related to "A Combination Inhibiting MEIS Proteins" which is developed to fulfill the objectives of the present invention are given in the enclosure wherein FIG. 1 is the view of inhibition of p21-Luciferase activity by MEISi-1.

Figure 2:
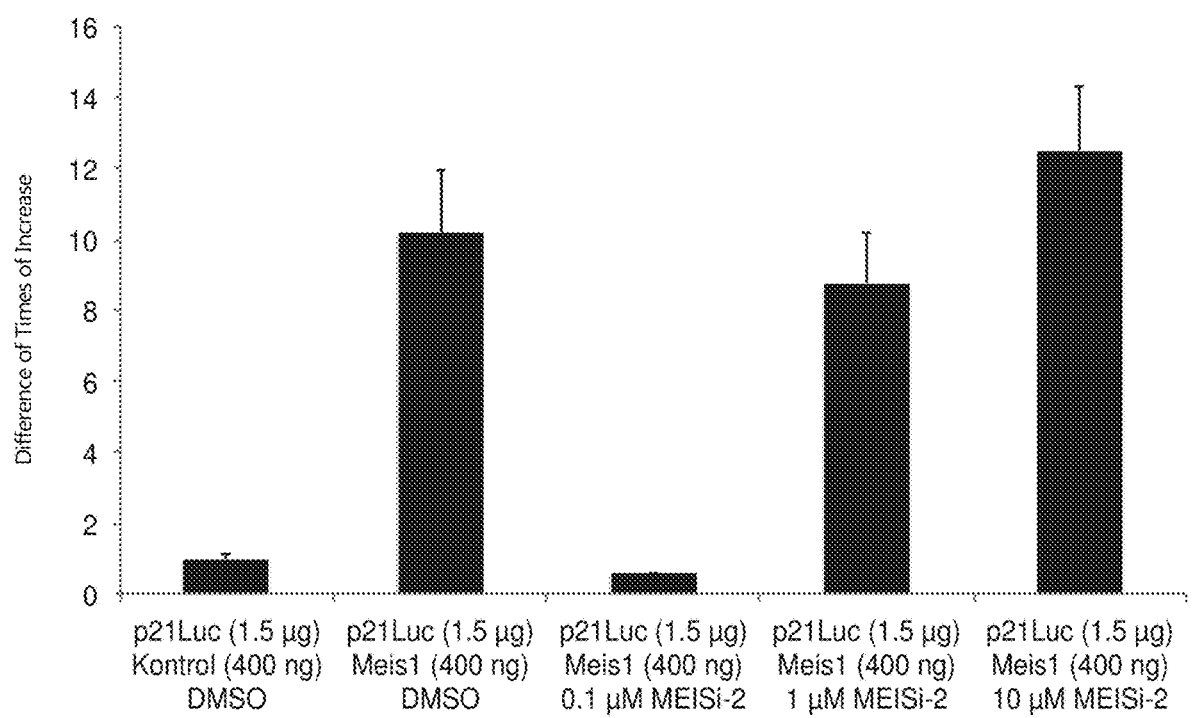

FIG. 2 is the view of inhibition of p21-Luciferase activity by MEISi-2.

Figure 3:
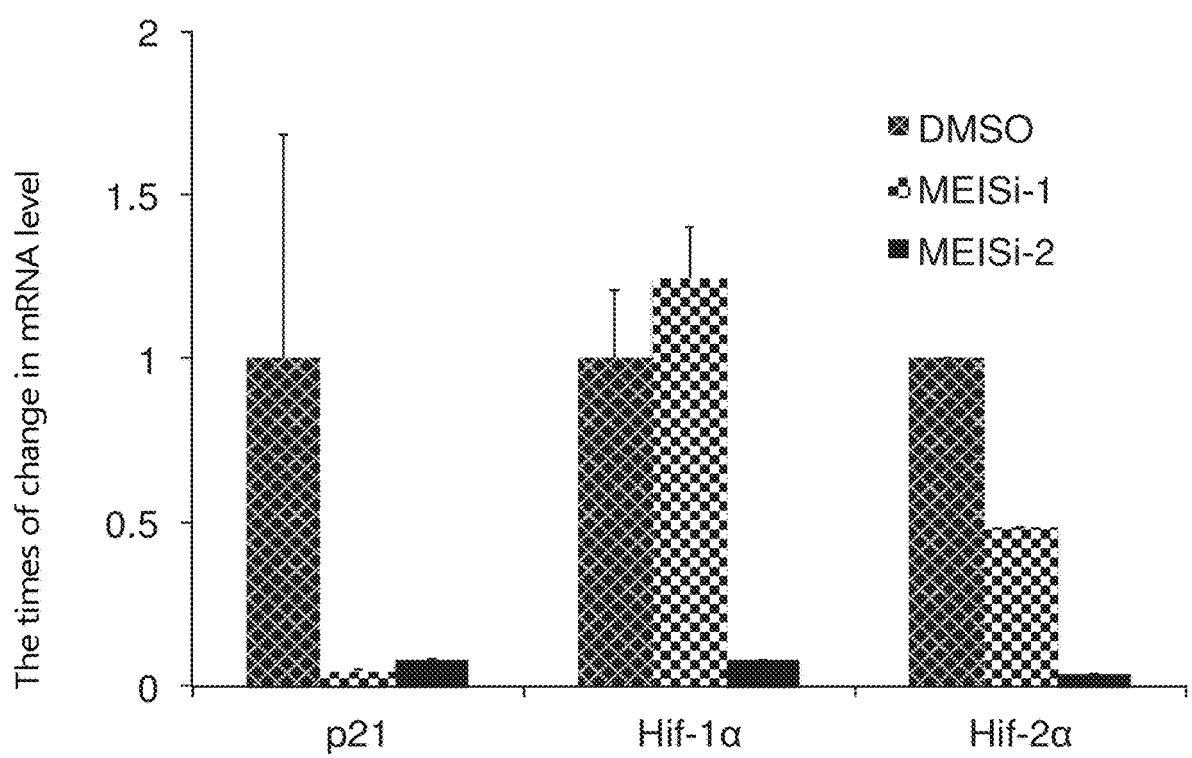

FIG. 3 is a view of a real time PCR analysis of the effects of MEIS inhibitors (MEISi-1 and MEISi-2) on Meis1 pathways (p21, Hif1a, Hif2a).

Figure 4:
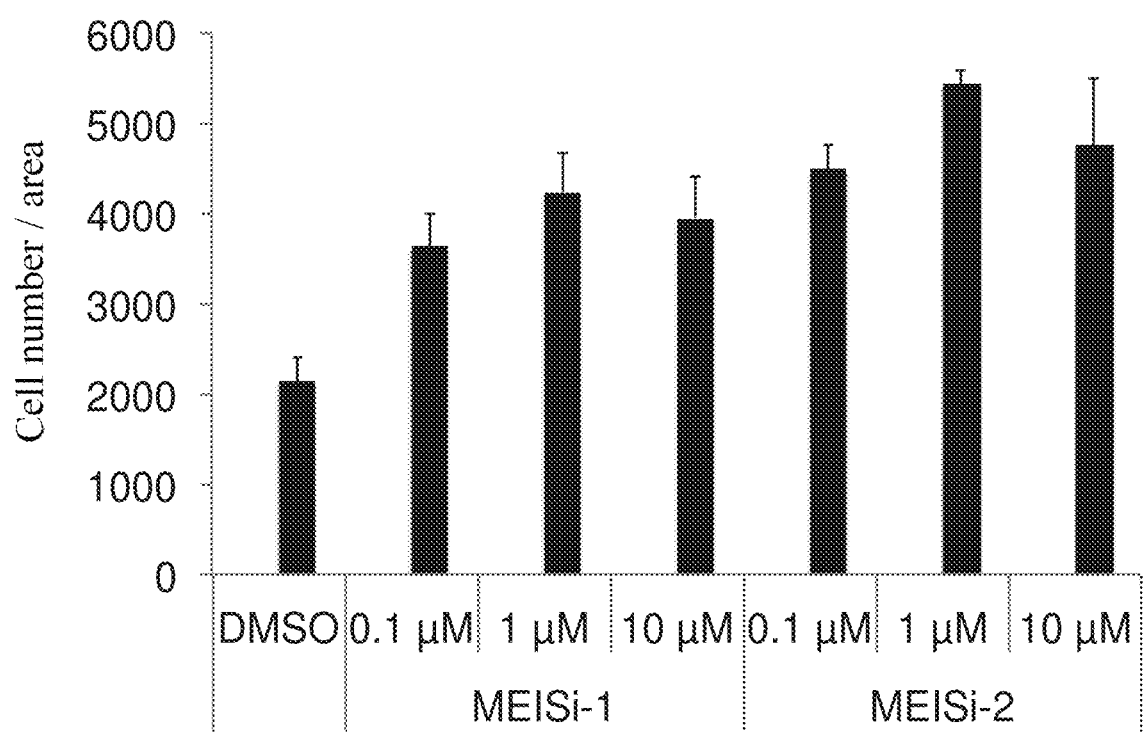

FIG. 4 is a view of a cytotoxicity analysis of MEIS inhibitors (MEISi-1 and MEISi-2) tried on L929 (murine fibroblast) cell line.

Figure 5:
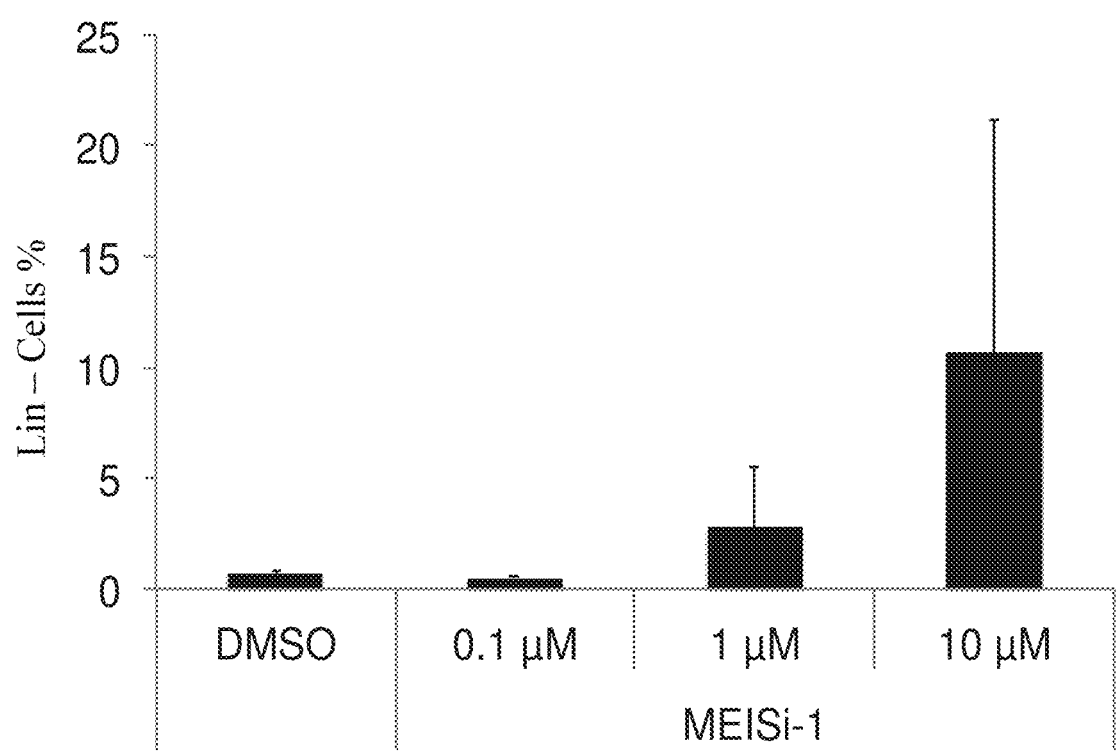

FIG. 5 is a view of the effect of MEIS inhibitors 7 days after administration thereof on dose dependent mouse hematopoietic cell proliferation.

Figure 6:
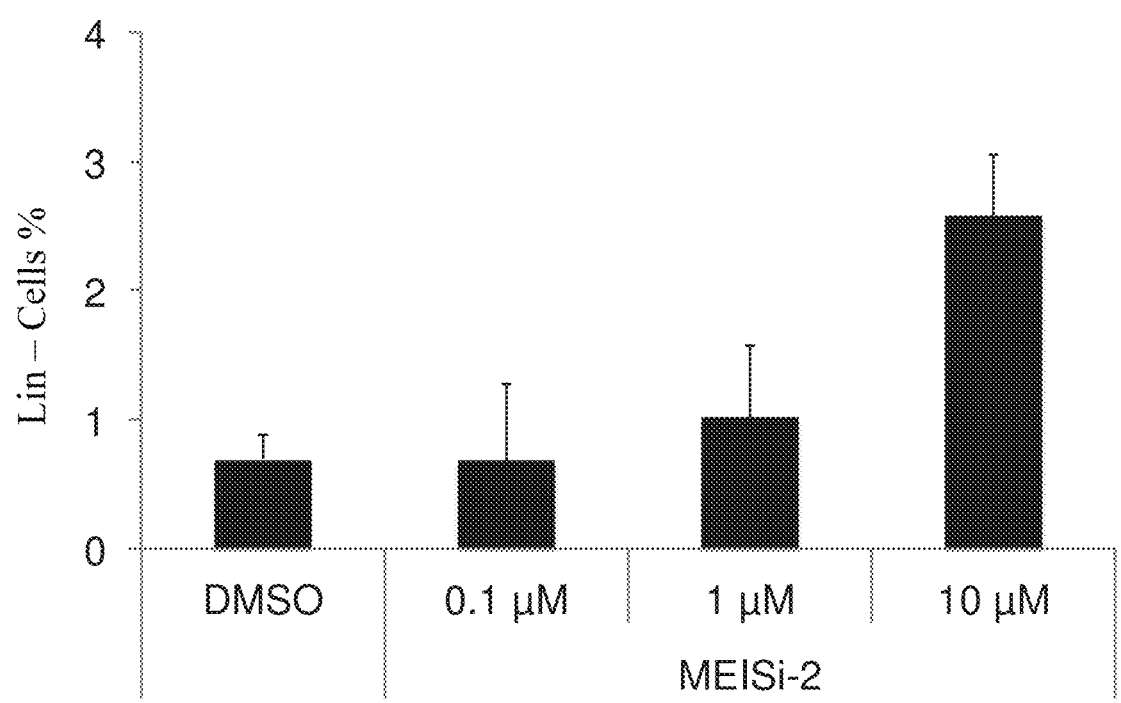

FIG. 6 is a view of the flow analysis of the cell count results of the effect of MEIS inhibitors on human hematopoietic cell proliferation.

Figure 7:
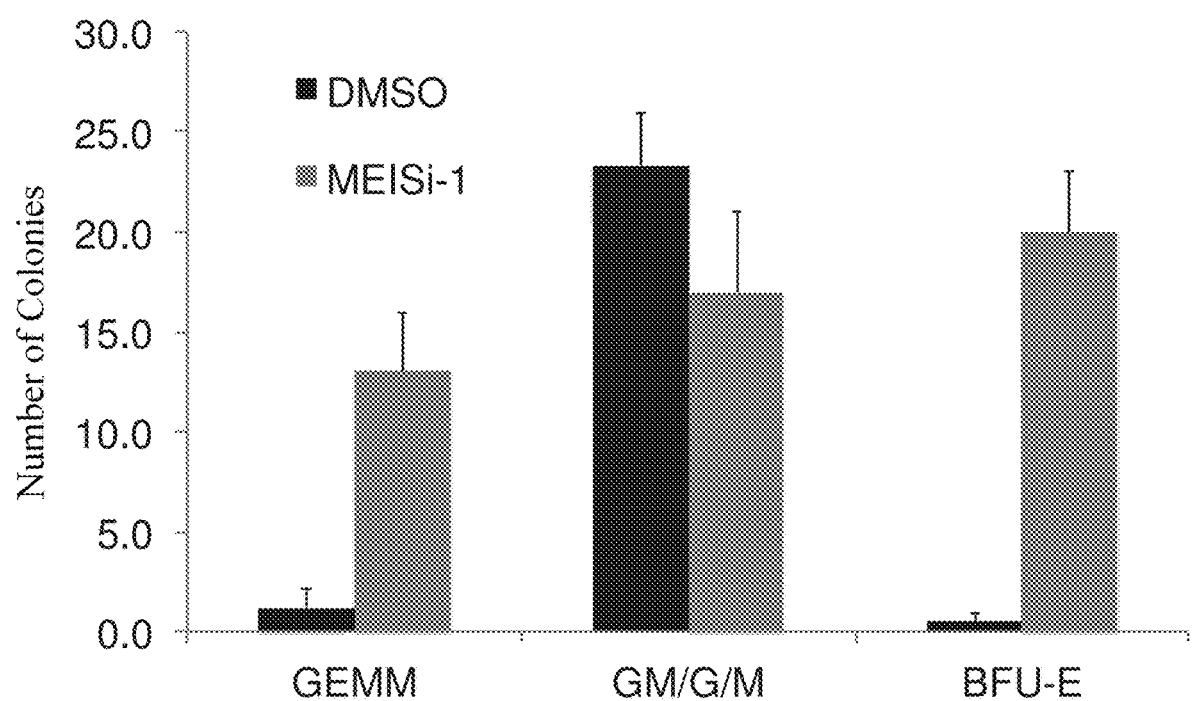
Figure 8A:
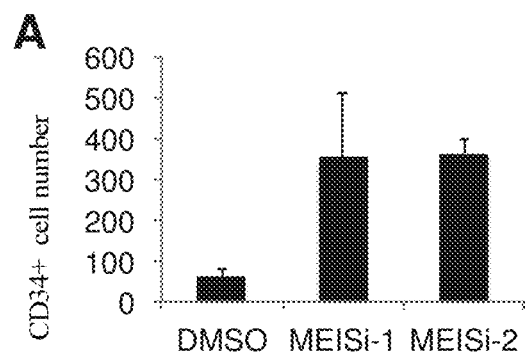
Figure 8B:
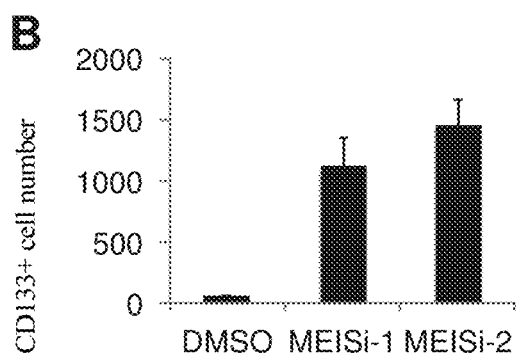
Figure 8C:
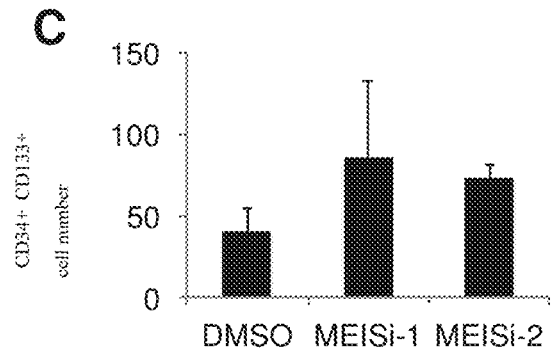
Figure 8D:
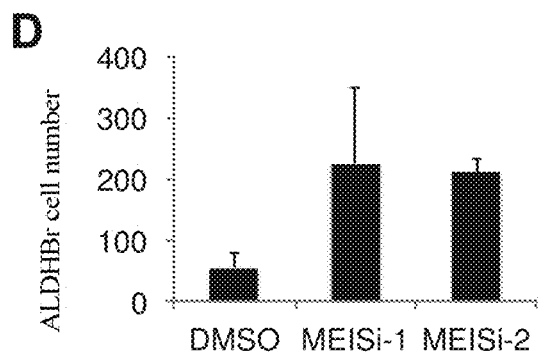

FIG. 7 is a view of the LSK flow analysis of MEISi-1 applied Lin− stem cells and progenitors isolated from bone marrow and obtained as a result of magnetic separation, and expansion thereof with MEISi-1 after 7 days.

FIGS. 8A, 8B, 8C and 8D is a view of the LSK flow analysis of MEISi-2 applied Lin− stem cells and progenitors isolated from bone marrow and obtained as a result of magnetic separation, and expansion thereof with MEISi-2 after 7 days;
 (A) CD34+, (B) CD133+, (C) CD34+CD133+, (D) ALDHbr antibodies.

Figure 9A:
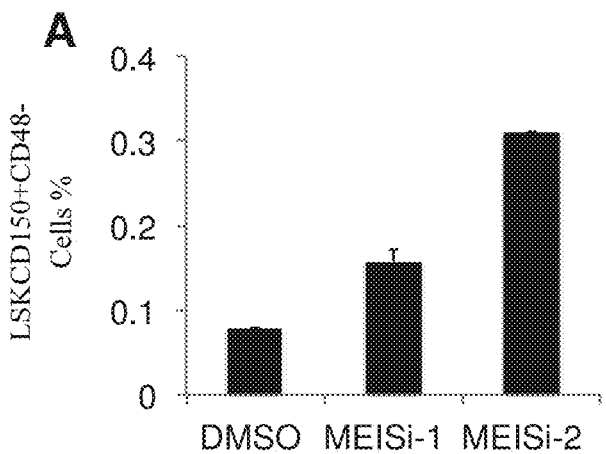
Figure 9B:
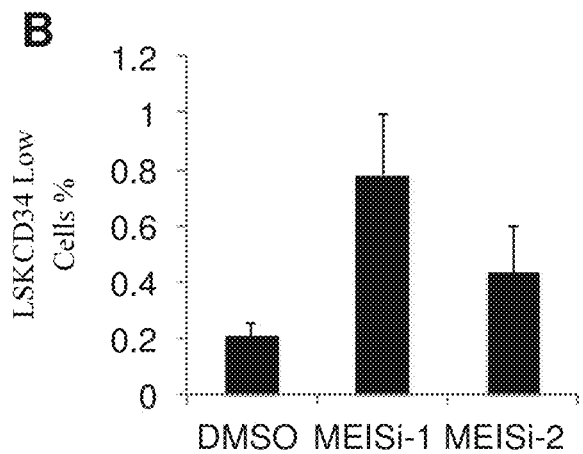

FIGS. 9A and 9B shows in vitro functional proliferation of mouse HSCs with CFU experiments and the ratios of different colonies that are formed;
 (A) LSKCD150+CD48− low HSCs,
 (B) LSKCD34 low HSCs.

Figure 10:
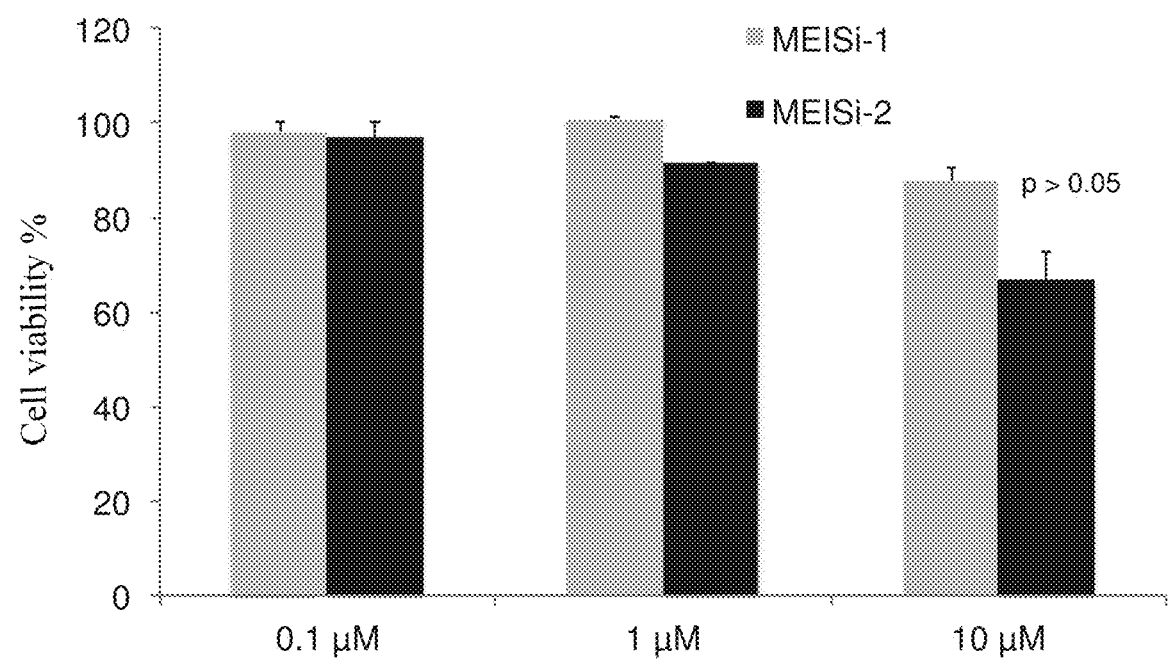

FIG. 10 shows the flow analysis of in vivo functional proliferation of the following cells 10 days after subcutaneous injection of the MEIS inhibitors MEISi-1 and MEISI-2 to the mouse.

DETAILED DESCRIPTION OF THE EMBODIMENTS

By means of in silico, in vitro and in vivo experiments, a formulation inhibiting MEIS proteins (Meis1, Meis2, Meis3) is obtained.
Experimental Studies
 The composition of the present invention comprises
 MEISi inhibitor,
 cells obtained as a result of isolation,
 medium,
 growth factor.
 MEISi inhibitor is comprised of MEISi-1 and MEISi-2.
 Accordingly, molarity calculation is made for MEISi-1 inhibitor taking as basis 4-[2-(benzylamino)-2-oxoethoxy]-N-(2,3-dimethylphenyl) benzamide with a molecular weight of 388.49 g/mol.
 The effective dose was determined to be 1 µM by means of the dose-dependent in vitro experiments.
 Molarity calculation was made for MEISi-2 inhibitor taking as basis 4-hydroxy-N'-[(Z)-(2-oxonaphthalen-1-ylidene)methyl] benzohydrazide with a molecular weight of 306.32 g/mol.
 The effective dose was determined to be 1 µM by means of the dose-dependent in vitro experiments.

The cells were obtained from mouse bone marrow, human bone marrow and human umbilical cord blood. These cells were incubated in Stem Span medium which is a serum-free culture medium.

Stem Span medium was used as the medium; and this medium contains bovine serum albumin, recombinant insulin, transferrin, 2-mercaptoethanol and nutrient-supplemented IMDM medium. pH value of this medium is 7.2. Stem Span medium is prepared freshly prior to each culture and enriched with growth factors.

The growth factors that are used are SCF which is hematopoietic stem cell factor, Flt3L which is fetus liver tyrosine kinase-3 ligand, and TPO which is thrombopoietin.
Characterization Studies In the combination of the present invention obtained by the above mentioned contents, the cells obtained as a result of isolation were seeded in a medium enriched with stem cell growth factors and treated with MEISi-1 or MEIS-2. Then, after incubation in 5% $CO_2$ and normal $O_2$ level at 37° C. for about 1 week to 10 days, proliferation of the cells were examined without a need for gene regulation technique. As a result of this proliferation, significant increases were observed and the results were supported by flow cytometry analyses.

The following characterization studies were conducted for MEIS inhibitors;
 1—in silico drug screening
 2—in vitro luciferase assays
 3—PCR pathway analyses
 4—ex vivo HSC expansion studies
 5—in vivo HSC expansion and
 6—cytotoxicity analyses
1—In Silico Drug Screening Against MEIS Homeodomain In order to perform in silico drug screening against MEIS, homeodomain has been analyzed for the amino acids interacting with the target DNA.

Two different paths are followed for determining the amino acids through which the MEIS homeodomain binds to TGACAG nucleotides:

a) Homolog/protected amino acid domains in the homeodomains of MEIS and the TALE proteins to which it belongs, and the protected amino acids for binding to the DNA were analyzed.

b) Pbx1 is a protein belonging to the same family as MEIS. Crystal structure of Pbx1 homoedomain was determined; three dimensional comparisons were made on this structure with the crystal structure of MEIS homeodomain; and the possible amino acids, by which MEIS homeodomain protein binds with the DNA, were analyzed.

Subsequently, gridbox was determined around the MEIS homeodomain amino acids, which are essential for binding to the DNA, and virtual inhibitor screening was performed.

Three dimensional structures of 1 million small molecules from the PubChem and ZINC database were obtained. Automated screening of 1 million molecules was carried out by using AutoDockVina 1.1.2 and PaDEL-ADV program and potential interaction parts were analyzed.

TABLE 1

Values of the homeodomain binding
energies of the MEISi inhibitors in kcal/mol.

| MEISi | MEIS Protein | PBX | PKNOX | TGIF1 | Average Difference |
|---|---|---|---|---|---|
| | | Homeodomain Binding Energy (kcal/mol) | | | |
| MEISi-1 | −7.2 | −6.2 | −6.4 | −6.2 | 0.9 |
| MEISi-2 | −6.9 | −6.5 | −6.5 | −6 | 0.7 |

Furthermore, the study that was conducted was compared with the other TALE homeodomains and binding energies thereof were determined, and thus MEIS-specific inhibitors were determined (Table 1).

2—Determining Meis1 Inhibitors by In Vitro Luciferase Reporter Assay

MEIS inhibitors were tested by conducting the luciferase reporter assay. It was observed that MEIS protein activated the luciferase reporters containing increasing doses of p21 promoters. pGL2 vectors comprising p21 gene promoter, which is activated by Meis1, were used in the luciferase assays. Therefore, 0.8 µg p21-pGL2, 400 ng Meis1 expression vector pCMVSPORT6-Meis1 (Open BioSystems) and 0.2 µg p CMV-LacZ (internal control) vector were transfected together to the COS cells. 4 hours later, the cells were treated with prototype MEIS inhibitors (at 0.1, 1 and 10 µM concentrations). 6-well plates and lipofectamine were used for transfection. 48 hours later, the cells were lysed, samples were collected and luciferase activity was determined. Reporter system of Promega (Promega Dual-Glo® Luciferase Assay System) was used for this. Luciferase measurements were normalized according to β-gal measurements (measurements were made at 420 nm). Thermo Lab system Lumino scan Ascent device was used for the luciferase measurements. As a result of these experimental studies, the in silico study, which targeted MEIS homeodomain and was conducted in comparison to the other TALE homeodomain, enabled to determine MEIS-specific hits (Experimental Results (ER): ER-A).

3—Testing MEIS Inhibitors by Real-Time RT-PCR

HSCs were prepared for each inhibitor (3 replicates in 6 wells) and cell series containing DMSO were used as control group. For each potential small molecule, assays were conducted at concentrations of 0.1, 1 and 10 µM; and the cells were trypsinized and collected after 3 days and were stored in trizol until RNA isolation was carried out. RNA isolation was performed by using Qiagen in RNeasy mini kit and protocol. cDNA was synthesized from 2 µg RNA by using Invitrogen in Superscript II RT system. Assays were conducted in BioRad CFX 96 Real Time PCR device by using SyberGreen (AppliedBiosystems). GAPDH was used as the control gene and was used for normalizing gene expression by ddCT method. Levels of the p21, Hif-1alpha (Hif-1α), Hif-2alpha (Hif-2α) gene expressions, which are known to be activated by Meis1, were determined and were controlled by DMSO control group (FIG. 3) (ER: B).

4—Determining the effect of MEIS inhibitor on ex vivo HSC proliferation

Bone marrow isolation from mouse and HSC purification were performed. For this, following euthanasia of 8-12 week old mice with isoflurane, bone marrow cells were obtained from femur and tibia bones. Briefly, Lin−, Sca1+, c-Kit+, CD34low cells (long term HSCs) were obtained by being stained with cell line cocktail with biotin (anti-CD3, anti-CDS, anti-B220, anti-Mac-1, anti-Gr1, anti-Ter119; Stem Cell Technologies), and that was followed by streptavidin-PE/Cy5.5, anti-Sca-1-FITC, anti-KIT-APC, and anti-CD34-PE staining. HSC medium known as SCF medium was used in the culture of the isolated bone marrow cells. SCF medium is comprised of serum-free Stem Span medium (Stem-Cell Technologies) into which are added 10 µg/ml heparin (Sigma-Aldrich), 10 ng/ml mouse SCF (R&D system), 20 ng/ml mouse TPO (R&D system), 20 ng/ml mouse IGF-2 (R&D system).

HSC frequency and number: The Lin− cells obtained from the bone marrow were treated in the cell culture with MEIS inhibitors or DMSO for 10 days, and subsequently the number of hematopoietic cells (FIG. 4) and the percentage of HSCs (FIGS. 5 and 6) were determined. In order to determine the number of HSCs, the concerned surface antigens (Lin−, Sca1+, c-Kit+, CD34−) were stained with fluorochrome conjugated antibody as in the previous studies and then analyzed with flow cytometry (ER: C).

In vitro functional proliferation of HSCs and the increasing colony numbers: After 7 days of cell culture, the number of HCSs treated with MEIS inhibitor or DMSO was determined. DMSO is the control group. 2000 cells were cultured in a suitable Semi-Solid Agar medium (Methocult, M3434, Stem Cell Technologies), and after 10-14 days, the number of colonies was determined and Colony Forming Unit Assay (CFU-Assay) was calculated. With the CFU assays, in vitro functional proliferation of HSCs, and the Granulocyte, Erythrocyte, Macrophage, Megakaryocyte (GEMM), Granulocyte Monocyte, (GM) and BFU-E ratios of the resulting different colonies were shown (FIG. 7) (ER: D).

Human HSC Expansion: The cells obtained from bone marrow or umbilical cord blood were separated by Percoll and mononuclear cells were obtained. They were transferred to the tubes containing HSC medium. HSC medium known as SCF medium was used in the culture of the isolated bone marrow and umbilical cord blood HSCs. SCF medium is comprised of serum-free Stem Span medium (Stem-Cell Technologies) containing human cytokine cocktail (StemSpan™ CC100, Stemcell Technologies, cat. no. 02690) and 1% PSA (10.000 units/ml penisilin and 10.000 ug/ml streptomycine and 25 µg/mL of Amphotericin B, Gibco, cat. no. 15240062). Following HSC purification, HSCs were seeded into a 96-well plate (Corning, 3799) at 200-300 HSCs per well; and upon adding maximum 200 µl of MEIS inhibitors mixed in SCF medium into each cell, they were incubated in 5% $CO_2$ and normal $O_2$ level at 37° C. for 7-10 days. Then, the number and percentage (frequency) of the HSCs and of the other hematopoietic progenitor cells were determined. The results were compared with the control group treated with DMSO (ER: E).

5—In Vivo Proliferation of HSCs with MEIS Inhibitors

As an alternative to ex vivo proliferation of HSCs by using small molecules, it was shown that application of MEIS inhibitors directly for in vivo HSC proliferation is also possible. The injected MEIS inhibitors were administered intraperitoneally in the range of 0.5 mg/kg to 10 mg/kg. In order to ensure effective incubation, the inhibitors were administered to the mice in 3 different doses; and 10 days after administration, the amount of the HSCs obtained from the bone marrow of the mice was determined (FIG. 9) (ER: F).

6—Cytotoxic Analyses of MEIS Inhibitors

L929 murine fibroblastic cell line was used for cytotoxic analyses of the MEIS inhibitors. The cells were seeded into a 96-well plate (Corning, 3799) at 2000 cells per well. The next day after seeding, the cells were treated by different doses by means of gradient concentration method using final concentrations of 0.1 µM, 1 µM, 10 µM with Meis1 inhibitor 1 (MEISi-1) and Meis1 inhibitor 2 (MEISi-2) mixed into each well in maximum 200 µl DMEM medium, and they were incubated in 5% $CO_2$ and normal $O_2$ level at 37° C. 4 days after the incubation, 10 µl WST1 cell proliferation solution (Boster, AR1159) was added, and after incubation of 4 hours, absorbance measurement was carried out at 450 nm by Thermo Lab system Multiskan Spektrum (ER-G).

Experimental Results

The experimental results were briefly named as (ER) and the concerned results are given below.

A—By means of the in vitro luciferase studies conducted, the MEIS inhibitors which we have named as MEIS inhibitor-1 (MEISi-1) and MEIS inhibitor-2 (MEISi-2) were determined for the first time. These inhibitors (MEISi-1 and MEISi-2) inhibit p21-Luc MEIS reporter in a dose-dependent manner (FIG. 1 and FIG. 2).

B—It was found that MEISi-1 and MEISi-2, which are among the developed MEIS inhibitors, reduce expression of p21, Hif-1alpha (Hif-1α), Hif-2alpha (Hif-2α) genes in the Meis1 pathway (FIG. 3).

C—Up to 2.5 times dose-dependent increase was determined in the number of hematopoietic cells treated with MEISi-1 and MEISi-2 after 10 days (FIG. 4). In treatment with MEISi-1, up to 10 times increase was observed in the number of HSCs (FIG. 5). This increase is dependent on the dose (FIG. 5). In addition, in Lin– cells treated with MEISi-2, up to 3 times increase was observed in the number of HSCs (FIG. 6).

D—It is observed from the increasing number of CFU-GEMM colonies that application of MEIS inhibitors increases the number of HSCs (FIG. 7). MEIS inhibitor effectively enables functional increase of the HSCs.

E—When all of the results are analyzed, it is observed that MEIS inhibitors trigger functional ex vivo proliferation of human HSCs (FIGS. 8A, 8B, 8C and 8D). When MEISi-1 and MEISi-2 were applied, CD34+ HSC number (FIG. 8A), CD133+ HSC number (FIG. 8B), CD34+CD133 HSC number (FIG. 8C) and ALDHBr HSC number (FIG. 8D) in human hematopoietic cell culture increased 2 times in comparison to DMSO control group.

F—It was demonstrated that in vivo application of MEISi-1 and MEISi-2 successfully increased HSC number in mouse bone marrow (FIG. 9A, LSKCD34low cells) and HSC number in the blood (FIG. 9B, LSKCD150+CD48– cells). In short, it was observed that MEIS inhibitors realized functional ex vivo proliferation of mouse and human HSCs (FIGS. 5-8D).

G—It was observed in the obtained results that MEIS inhibitors MEISi-1 MEISi-2 are not cytotoxic in 0, 1, 1 and 10 µM doses (FIG. 10).

As a result, MEIS inhibitors were determined for the first time in the studies conducted. In silico studies, which target MEIS homeodomain and are conducted in comparison to the other TALE homeodomains, have enabled to determine MEIS-specific hits (Table 1).

These inhibitors
inhibit p21-Luc MEIS reporters. (FIG. 1 and FIG. 2)
reduce expression of the genes in Meis1 pathway. (FIG. 3)
MEIS inhibitors trigger ex vivo proliferation of mouse and human functional HSCs (FIGS. 4, 5, 6, 7, 8A, 8B, 8C and 8D).

It was shown that in vivo application of MEISi-1 and MEISi-2 increased the number of HSCs in bone marrow and peripheral blood (FIGS. 9A and 9B).

It was determined that MEIS inhibitor 1 (MEISi-1) and MEIS inhibitor 2 (MEISi-2) are not cytotoxic (FIG. 10).

APPLICATION OF THE INVENTION

The invention realizes in vitro and ex vivo proliferation of the umbilical cord stem cells and human bone marrow stem cells. Furthermore, by means of the invention; single cell expansion is stimulated after single hematopoietic stem cell selection after gene regulation, and expansion of the hematopoietic stem cells obtained from adult tissues and embryonic cells is enabled. Additionally; expansion of resident cardiac stem cells and cardiomyocytes; ex vivo expansion of mononuclear cells prior to bone marrow transplantation; ex vivo expansion of fibroblast, cartilage, endothelial, limbal and mesenchymal stem cells; MEIS inhibition in cancer and cancer stem cells highly expressing MEIS gene family are enabled.

What is claimed is:

1. A combination for inhibiting MEIS proteins, the combination comprising: isolated cells, a medium, growth factors and MEISi inhibitor, wherein the MEISi inhibitor comprises MEISi-1 having a chemical formula of 4-[2-(benzylamino)-2-oxoethoxy]-N-(2,3-dimethylphenyl) benzamide or MEISi-2 having a chemical formula of 4-hydroxy-N'-[(Z)-(2-oxonaphthalen-1-ylidene)methyl] benzohydrazide.

2. The combination according to claim 1, wherein the isolated cells are isolated from mouse bone marrow, human bone marrow and human umbilical cord blood.

3. The combination according to claim 1, wherein the medium has a pH value of 7.2 and contains bovine serum albumin, recombinant insulin, transferrin, 2-mercaptoethanol and IMDM medium.

4. The combination according to claim 1, wherein the growth factors are hematopoietic stem cell factor SCF, fetus liver tyrosine kinase-3 ligand Flt3L, and thrombopoietin.

5. The combination according to claim 1, wherein the combination comprises MEISi-1.

6. The combination according to claim 1, wherein the combination comprises MEISi-2.

7. A method of expansion of hematopoietic stem cells, comprising: using the combination of claim 1 to expand the hematopoietic stem cells; wherein the hematopoietic stem cells are obtained from adult tissues and embryonic cells, resident cardiac stem cells and cardiomyocytes.

8. A method of ex vivo expansion of isolated cells prior to bone marrow transplantation and ex vivo expansion of fibroblast, cartilage, endothelial, limbal and mesenchymal stem cells, comprising: using the combination of claim 1 to ex vivo expand the isolated cells prior to the bone marrow transplantation, wherein the isolated cells are mononuclear cells, fibroblast, cartilage, endothelial, limbal or mesenchymal stem cells.

9. A method of inhibiting cancer and MEIS proteins in cancer stem cells, comprising using the combination of claim 1 to inhibit the cancer and the MEIS proteins.

10. The combination according to claim 2, wherein the medium has a pH value of 7.2 and contains bovine serum albumin, recombinant insulin, transferrin, 2-mercaptoethanol and IMDM medium.

11. The combination according to claim 2, wherein the growth factors are hematopoietic stem cell factor SCF, fetus liver tyrosine kinase-3 ligand Flt3L, and thrombopoietin.

12. The combination according to claim 3, wherein the growth factors are hematopoietic stem cell factor SCF, fetus liver tyrosine kinase-3 ligand Flt3L, and thrombopoietin.

13. The combination according to claim 2, wherein the combination comprises MEISi-1.

14. The combination according to claim 3, wherein the combination comprises MEISi-1.

15. The combination according to claim 4, wherein the combination comprises MEISi-1.

16. The combination according to claim 2, wherein the combination comprises MEISi-2.

17. The combination according to claim 3, wherein the combination comprises MEISi-2.

18. The combination according to claim 4, wherein the combination comprises MEISi-2.

19. The combination according to claim 5, wherein the combination comprises MEISi-2.

20. The combination according to claim 10, wherein the growth factors are hematopoietic stem cell factor SCF, fetus liver tyrosine kinase-3 ligand Flt3L, and thrombopoietin.

\* \* \* \* \*